(12) United States Patent
Tupil et al.

(10) Patent No.: US 10,028,850 B2
(45) Date of Patent: Jul. 24, 2018

(54) ENDOPROSTHESIS WITH FILAMENT REPOSITIONING OF RETRIEVAL MEMBER AND GUARD STRUCTURE

(71) Applicant: Boston Scientific Scimed Inc., Maple Grove, MN (US)

(72) Inventors: Srinath Tupil, Acton, MA (US); James Biggins, Waltham, MA (US); William Bertolino, Framingham, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 692 days.

(21) Appl. No.: 14/336,825

(22) Filed: Jul. 21, 2014

(65) Prior Publication Data

US 2014/0330364 A1 Nov. 6, 2014

Related U.S. Application Data

(63) Continuation of application No. 12/872,298, filed on Aug. 31, 2010, now Pat. No. 8,784,473.

(Continued)

(51) Int. Cl.
*A61F 2/06* (2013.01)
*A61F 2/88* (2006.01)
*A61F 2/07* (2013.01)
*A61F 2/86* (2013.01)
(Continued)

(52) U.S. Cl.
CPC .................. *A61F 2/88* (2013.01); *A61F 2/07* (2013.01); *A61F 2/86* (2013.01); *A61F 2/90* (2013.01);
(Continued)

(58) Field of Classification Search
CPC ........ A61F 2/07; A61F 2/2418; A61F 2/2427; A61F 2/243; A61F 2/2439; A61F 2/2466;
(Continued)

(56) References Cited

U.S. PATENT DOCUMENTS 5,843,158 A 12/1998 Lenker et al.
6,042,605 A 3/2000 Martin et al.
(Continued)

FOREIGN PATENT DOCUMENTS

JP 2008-519668 A 6/2008
WO 2006/053270 A2 5/2006
(Continued)

*Primary Examiner* — Katherine M Shi
(74) *Attorney, Agent, or Firm* — Seager, Tufte & Wickhem, LLP

(57) ABSTRACT

An endoprosthesis includes a stent structure having an elongate member longitudinal portions of which overlap to define the crossover structures. The stent structure may also include loop structures, which are contiguous with the crossover structures, through which a filament extends. A guard structure is secured to the stent structure and located adjacent to the crossover structures to obstruct displacement of the filament between the longitudinal portions of the elongate member of the crossover structures. A method for operating the endoprosthesis includes displacing the loop structures toward one another along the filament to displaced positions relative to the suture structure for reducing the respective profiles of the stent structure and patch structure.

20 Claims, 4 Drawing Sheets

Related U.S. Application Data

(60) Provisional application No. 61/241,206, filed on Sep. 10, 2009.

(51) Int. Cl.
*A61F 2/90* (2013.01)
*A61F 2/95* (2013.01)

(52) U.S. Cl.
CPC ... *A61F 2002/072* (2013.01); *A61F 2002/075* (2013.01); *A61F 2002/9505* (2013.01); *A61F 2002/9511* (2013.01); *A61F 2002/9528* (2013.01); *A61F 2002/9534* (2013.01); *A61F 2220/0058* (2013.01); *A61F 2220/0075* (2013.01); *A61F 2230/0078* (2013.01); *A61F 2250/0039* (2013.01)

(58) Field of Classification Search
CPC .... A61F 2/844; A61F 2/95; A61F 2/86; A61F 2/88; A61F 2/962; A61F 2002/072; A61F 2002/075; A61F 2002/2484; A61F 2002/9511; A61F 2002/9522; A61F 2002/9528; A61F 2002/9534; A61F 2002/9505; A61F 2002/823; A61F 2220/0075; A61F 2220/0058; A61F 2250/0039; A61F 2/82; A61F 2/856; A61F 2/89; A61F 2/90; A61F 2/915; A61F 2/94

USPC ...................... 623/1.12, 1.15, 1.33
See application file for complete search history.

(56) References Cited

U.S. PATENT DOCUMENTS

| | | |
|---|---|---|
| 6,086,610 A | 7/2000 | Duerig et al. |
| 6,656,216 B1 | 12/2003 | Hossainy et al. |
| 6,878,161 B2 | 4/2005 | Lenker |
| 8,206,427 B1 * | 6/2012 | Ryan ............... A61F 2/07 623/1.11 |
| 2003/0225445 A1 | 12/2003 | Derus et al. |
| 2006/0116752 A1 | 6/2006 | Norton et al. |
| 2006/0190070 A1 * | 8/2006 | Dieck ............... A61F 2/90 623/1.12 |
| 2006/0190075 A1 * | 8/2006 | Jordan ............... A61F 2/90 623/1.23 |
| 2008/0125845 A1 | 5/2008 | Fischer et al. |
| 2009/0187240 A1 * | 7/2009 | Clerc ............... A61F 2/07 623/1.17 |

FOREIGN PATENT DOCUMENTS

| | | |
|---|---|---|
| WO | 2006/053270 A3 | 8/2006 |
| WO | 2006/123046 A1 | 11/2006 |

\* cited by examiner

ENDOPROSTHESIS WITH FILAMENT REPOSITIONING OF RETRIEVAL MEMBER AND GUARD STRUCTURE

CROSS-REFERENCE TO RELATED APPLICATION

This application is a continuation of U.S. application Ser. No. 12/872,298, filed on Aug. 31, 2010, which claims the benefit of U.S. Provisional Application No. 61/241,206, filed Sep. 10, 2009, the contents of all of which are incorporated by reference herein.

FIELD OF THE INVENTION

The present invention relates generally to an endoprosthesis and, more specifically, to an endoprosthesis including a stent structure and a guard structure secured thereto for obstructing tangling of a suture structure with the stent structure.

BACKGROUND OF THE INVENTION

An endoprosthesis is implantable in the body of the patient, such as a blood vessel, or other body cavity, such as non-vascular orifices and/or lumens. The endoprosthesis includes a medical structure, such as a stent, which may be braided. A braided stent may include loop structures and adjacent crossover structures. The crossover structures include longitudinal portions of the elongate members of the braided stent which overlap one another and may be in direct contact. A suture structure may extend through the loop structures to, for example, provide for the cinching of the stent structure. Cinching of the stent structure may be desired to reduce the profile thereof for insertion in and displacement through a vessel in the body of a patient.

Manipulation of the suture structure in the stent structure may cause the suture structure to approach the crossover structures and directly contact the longitudinal portions of the elongate members which overlap. The direct contact of the suture structure with the overlapping longitudinal portions of the elongate members may result in the suture structure becoming tangled therewith. Alternatively, the suture structure may be drawn into direct contact with the longitudinal portions of the elongate members with sufficient force and the elongate members may be sufficiently resilient such that the direct contact of the suture structure forces the elongate members apart to provide a path for the suture structure to translate through the crossover structure. Neither of the scenarios is typically desirable since the suture structure is normally intended to remain within the loop structures through which the suture structure initially extends. Accordingly, displacement of the suture structure through the crossover structure is normally not desirable. Also, tangling of the suture structure with the stent structure is normally undesirable since substantially unimpeded displacement of the suture structure relative to the stent structure is typically preferred.

SUMMARY OF THE INVENTION

The endoprosthesis of the present invention includes a stent structure having loop structures through which a suture structure extends. The stent structure has crossover structures which are contiguous to the loop structures. The stent structure has an elongate member longitudinal portions of which overlap to define the crossover structures. A guard structure is secured to the stent structure and located adjacent to the crossover structures to obstruct displacement of the suture structure between the longitudinal portions of the elongate member of the crossover structures. A method for operating the endoprosthesis includes displacing the loop structures toward one another along the suture structure to displaced positions relative to the suture structure for reducing the respective profiles of the stent structure and guard structure. The loop structures are secured in the displaced positions to retain the profiles of the stent structure and guard structure which are reduced.

The guard structure and location thereof adjacent to the crossover structure obstructs the suture structure from directly contacting the overlapping portions of the elongate member in the crossover structure. The obstruction provided by the guard structure reduces the likelihood of the suture structure becoming entangled with the overlapping portions of the elongate member. Preventing the suture structure from becoming tangled with the elongate member of the braided stent structure is normally desirable. Also, the obstruction provided by the guard structure reduces the likelihood of the suture structure forcing apart the overlapping portions of the elongate member and translating through the crossover structure. Preventing the suture structure from displacing through the crossover structure is normally desirable.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
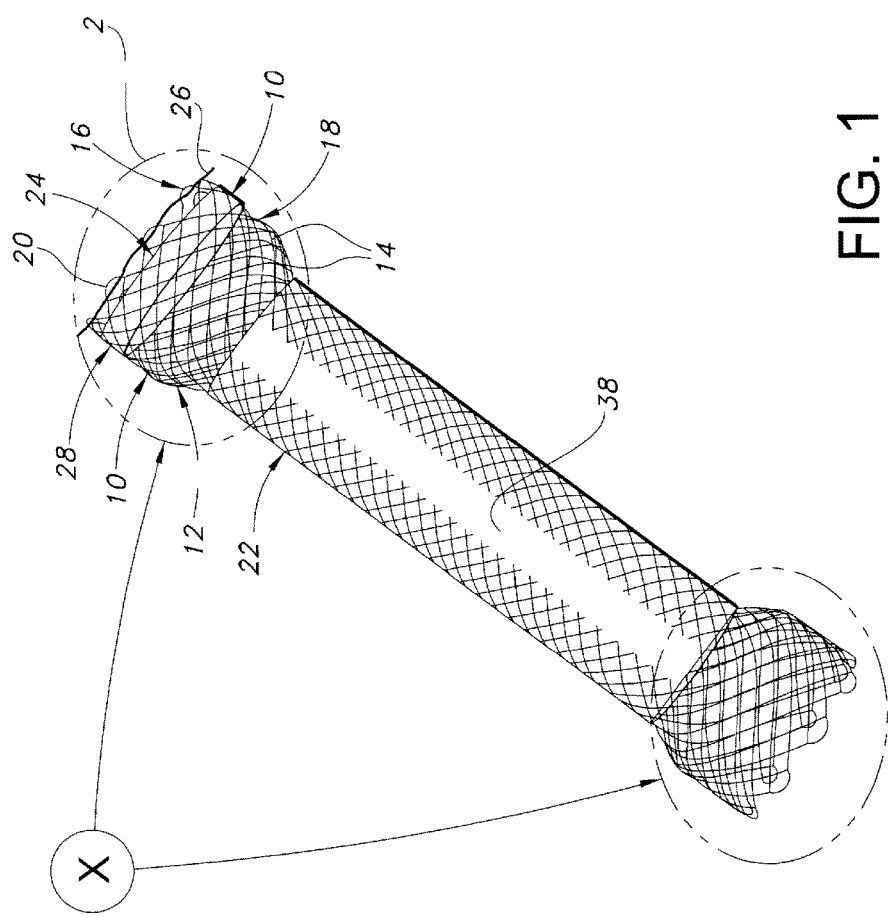
FIG. 1 is a perspective view of the endoprosthesis of the present invention, the endoprosthesis being shown as including a braided stent structure which is partially covered, and a ring structure secured to the stent structure.
Figure 2:
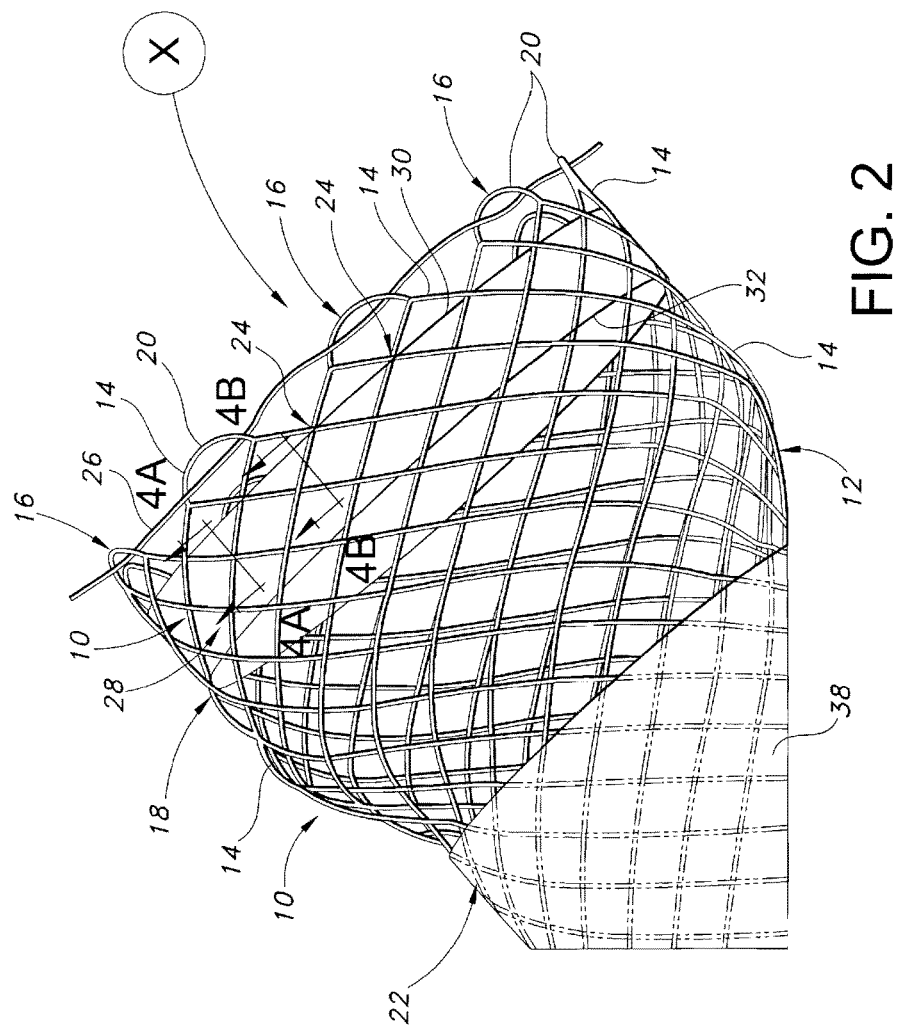
FIG. 2 is an enlarged view of the circled portion 2 of FIG. 1 showing the ring structure located adjacent to the crossover structures of the stent structure, the stent structure being shown as including loop structures through which a suture structure extends.

Referring to the drawings and more specifically to FIGS. 1 and 2, the endoprosthesis 10 includes a stent structure 12 having elongate members 14 which are braided into a tubular structure. In an alternative embodiment, the tubular structure is braided from a single elongate member 14. The stent structure 12 may include a one over and a one under braided pattern of elongate members or filaments 14. Even so, the invention is applicable to any type of stent structure comprising at least one crossover point where one or more elongate members intersect. For example, stent having at least one crossover point may include without limitation, a braided stent, a wound stent, a helically wound stent, a knitted stent, a woven stent, and the like. Furthermore, the invention is not limited to stents; it pertains to any endoprosthesis comprising elongate members and a crossover point where one or more elongate members intersect.

The stent structure 12 may include loop structures 16 which are defined by longitudinal portions of the elongate members 14. The portions of the elongate members 14 which define the loop structures 16 are welded to adjacent portions of the elongate members 14, as shown in FIG. 2. In an alternative embodiment, the loop structures 16 may be defined by longitudinal portions of a single elongate member 14 which are continuous.

The stent structure 12 has an end portion 18 which includes end surfaces 20 which are defined by sections of the loop structures 16. The end portion 18 has a transverse dimension which is generally constant along the longitudinal axis of the stent structure 12. The transverse dimension of the end portion 18 corresponds to the diameter thereof from the tubular shape of the stent structure 12.

The stent structure 12 includes an intermediate portion 22 having a transverse dimension, i.e., diameter, which is generally constant along the longitudinal axis of the stent structure 12. The transverse dimension of the intermediate portion 22 corresponds to the diameter thereof from the tubular shape of the stent structure 12. The diameter of the intermediate portion 22 is smaller than the diameter of the end portion 18. The portion of the stent structure 12 between the intermediate portion 22 and end portion 18 is flared to accommodate the different diameters of the end portion 18 and intermediate portion 22.

The stent structure 12 includes crossover structures 24 which are located longitudinally relative to the stent structure between the end surface 20 and intermediate portion 22. The crossover structures 24 include longitudinal portions of the elongate members 14 which overlap one another and may be in direct contact. The overlapping portions of the elongate members 14 extend in respective directions which are different and thereby cause the overlapping portions to appear to intersect as viewed from the perspective of FIG. 2.

The overlapping relation of the elongate members 14 in the crossover structures 24 allows relative movement between the elongate members therein. The relative movement and flexibility of the elongate members 14 allows transverse expansion and contraction of the stent structure 12. The transverse expansion and contraction of the stent structure 12 corresponds to radial expansion and contraction from the tubular shape of the stent structure 12.

The flexibility and resiliency of the elongate members 14 may result in the radial separation thereof in the crossover structures 24 when the elongate members are subjected to forces which are sufficiently large and directed to the respective elongate members 14 in suitably opposite directions.

The stent structure 12 may be formed of any suitable implantable material, including without limitation nitinol, stainless steel, cobalt-based alloy such as Elgiloy®, platinum, gold, titanium, titanium alloys, tantalum, niobium, polymeric materials and combinations thereof. Useful polymeric materials may include, for example, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, natural silk, polyvinyl chloride, polytetrafluoroethylene, including expanded polytetrafluoroethylene (ePTFE), fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, and copolymers and combinations thereof. Further, useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly (L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly (phosphate ester) and the like. Wires made from polymeric materials may also include radiopaque materials, such as metallic-based powders, particulates or pastes which may be incorporated into the polymeric material. For example the radiopaque material may be blended with the polymer composition from which the polymeric wire is formed, and subsequently fashioned into the stent as described herein. Alternatively, the radiopaque material and/or radiopaque markers may be applied to the surface of the metal or polymer stent. In either embodiment, various radiopaque materials and their salts and derivatives may be used including, without limitation, bismuth, barium and its salts such as barium sulphate, tantulaum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent may be selectively made radiopaque at desired areas along the wire or made be fully radiopaque, depending on the desired end-product and application. Further, the stent filaments may have an inner core of tantalum, gold, platinum, iridium or combination of thereof and an outer member or layer of nitinol to provide a composite wire for improved radiocapicity or visibility. Desirably, the inner core is platinum and the outer layer is nitinol. More desirably, the inner core of platinum represents about at least 10% of the wire based on the overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Patent Application Publication 2002/0035396 A1, the contents of which is incorporated herein by reference. Preferably, the stent filaments are made from nitinol, or a composite wire having a central core of platinum and an outer layer of nitinol.

The stent 12 may be capable of radially expanding by radial or circumferential distension or deformation. The stent 12 may self-expand at one or more specific temperatures as a result of the memory properties of the material included in the stent for a specific configuration. Nitinol is a material which may be included in the stent 12 for providing radial expansion thereof by the memory properties of the nitinol based on one or more specific temperatures or the superelastic properties of nitinol.

The endoprosthesis may include a cover or liner 38. The cover or liner 38 may be disposed over portions of the stent 12. As depicted in FIG. 1, the cover or liner 38 may be disposed along the intermediate portion 22 of the stent 12 or along a portion or portions of the intermediate portion 22. The cover or liner 38 may be a coating of a polymeric material. For example, the stent wires may be partially or fully covered with a biologically active material which is elutably disposed with the polymeric material. Further, the polymeric coating may extend over or through the interstitial spaces between the stent wires so as to provide a hollow tubular liner or cover over the interior or the exterior surface of the stent, thereby providing a stent-graft device. The polymeric material may be selected from the group consisting of polyester, polypropylene, polyethylene, polyurethane, polynaphthalene, polytetrafluoroethylene, expanded polytetrafluoroethylene, silicone, and combinations thereof. The covering may be in the form of a tubular structure. The silicone covering may be suitably formed by dip coating the stent. Details of such dip coating may be found in U.S. Pat. No. 5,875,448, the content of which is incorporated herein by reference. The present invention is not limited to forming the silicone film by dip coating, and other techniques, such as spraying, may suitably be used. After applying the silicone coating or film to the stent, the silicone may be cured. Desirably, the curing is low temperature curing, for example from about room temperature to about 90° C. for a short period of time, for example from about 10 minutes or more to about 16 hours. The cured silicone covering may also be sterilized by electronic beam radiation, gamma radiation ethylene oxide treatment and the like. Further details of the curing and/or sterilization techniques may be found in U.S. patent application Ser. No. 6,099,562, the content of which is incorporated herein by reference. Argon plasma treatment of the cured silicone may also be used. Argon plasma treatment of the cured silicone modifies the surface to the cured silicone to, among other things, make the surface less sticky. The invention, however, is not limited to stent-graft devices having polymeric coatings. The graft portion may suitably be formed from polymeric films, polymeric tapes, polymeric tubes, polymeric sheets and textile materials. Textile material may be woven, knitted, braided and/or filament wound to provide a suitable graft. Various biocompatible polymeric materials may be used as textile materials to form the textile structures, including polyethylene terephthalate (PET), naphthalene dicarboxylate derivatives such as polyethylene naphthalate, polybutylene naphthalate, polytrimethylene naphthalate, trimethylenediol naphthalate, ePTFE, natural silk, polyethylene and polypropylene, among others. Moreover, textile materials and stent materials may be co-formed, for example co-braided, to form a stent-graft device.

The endoprosthesis 10 includes a suture structure 26 which may be defined by a filament which extends through the loop structures 16, as shown in FIG. 2. The extension of the suture structure or filament 26 through the loop structures 16 provides for the cinching of the end portion 18 by displacing the loop structures 16 toward one another along the suture structure or filament 26. The cinching reduces the diameter of the end portion 18 which reduces the profile thereof. The cinching of the end portion 18 is allowed by the resilience of the elongate members 14. Also, the resilience of the elongate members 14 resists the contraction caused by the cinching such that the release thereof results in the elongate members 14 urging the end portion 18 to expand to the diameter thereof before the cinching. Return of the end portion 18 to the diameter thereof before the cinching is possible in the absence of any obstructions to the expansion of the end portion.

The reduction of the profile of the end portion 18 facilitates insertion of the end surfaces 20 into a vessel in the body of a patient, and the subsequent displacement of the stent structure 12 through the vessel. Following the positioning of the stent structure 12 at the desired location within the vessel, the cinching of the end portion 18 is released which results in the elongate members 14 urging the end portion 18 to expand to the diameter thereof before the cinching. Obstructions located in the vessel may prevent the end portion 18 from expanding to the diameter thereof before the cinching. The complete return of the end portion 18 to the diameter thereof before the cinching is possible in the absence of obstructions in the vessel.

The insertion and displacement of the stent structure 12 into and through the vessel may be provided by inserting the suture structure or filament 26 into the vessel before the insertion of the stent structure 12 therein. Subsequently, the suture structure or filament 26 may be translated through the vessel sufficiently to draw the end surfaces 20 into and through the vessel. The translation of the suture structure or filament 26 through the vessel may be continued to draw the stent structure 12 to the desired location in the vessel.

Various biocompatible polymeric materials may be used for the suture structure or filament 26, including polyethylene terephthalate (PET), naphthalene dicarboxylate derivatives such as polyethylene naphthalate, polybutylene naphthalate, polytrimethylene naphthalate, trimethylenediol naphthalate, ePTFE, natural silk, polyethylene and polypropylene, among others. Moreover, the filament 26 may be or may include a metallic strand or strands. The metallic strands or strands may include any suitable implantable metallic material, including without limitation nitinol, stainless steel, cobalt-based alloy such as Elgiloy®, platinum, gold, titanium, titanium alloys, tantalum, niobium and combinations or alloys thereof. The suture structure or filament 26 may be monofilament, multifilament or combinations thereof. Further, the suture structure or filament 26 may include twisted or non-twisted filaments.

The endoprosthesis 10 includes a guard structure 28 having outer and inner edges 30, 32, as shown in FIG. 2. As depicted in FIG. 2, the guard structure 28 is in a form of a ring or circular band. The guard or ring structure 28 is secured to the inner surface of the stent structure 12 such that the guard or ring structure has a transverse orientation relative to the stent structure. The guard or ring structure 28 is oriented relative to the stent structure 12 such that the inner edge 32 is located between the intermediate portion 22 and outer edge 30. Also, the orientation of the guard or ring structure 28 relative to the stent structure 12 provides for the outer edge 30 to intersect the crossover structures 24, as viewed from the perspective of FIG. 2.

The location of the guard or ring structure 28 adjacent to the crossover structures 24 obstructs displacement of the suture structure 26 to the longitudinal portions of the elongate members 14 which overlap in the crossover structures 24. The displacement begins with the suture structure 26 being located within the loop structure 16 and translated in the direction toward the crossover structures 24 and intermediate portion 22. The guard or ring structure 28 obstructs the suture structure 26 from becoming lodged between the overlapping portions of the elongate member 14 as a result of displacement of the suture structure in a direction toward the intermediate portion 22. Also, the guard or ring structure 28 obstructs the suture structure 26 from becoming tangled with or translating through the region between the overlapping portions of the elongate member 14 in the crossover structures 24. Translation of the suture structure 26 between the overlapping portions of the elongate members 14 in the crossover structures 24 may result from radial separation of the overlapping portions which may be provided by the resilience thereof and radial separation forces provided by the forced displacement of the suture structure 26 in the axial direction relative to the stent structure 12.

The guard or ring structure 28 may have a resilience which is sufficiently limited to resist transverse compression thereof. Consequently, the guard or ring structure 28 resists the cinching of the end portion 18 by the suture structure 26. The resilience of the guard or ring structure 28 is sufficient to allow the cinching of the end portion 18. Consequently, the cinching provides for the transverse compression of the end portion 18 and guard or ring structure 28 from an original transverse dimension to a reduced transverse dimension thereof. When the cinching of the end portion 18 is released, the guard or ring structure 28 urges the end portion 18 to return to the original transverse dimension.

The guard structure 28 may be formed of the same material as the covering or liner 38. The guard structure 28 may be formed in conjunction with the cover or liner 38, for example by selective coating and or coating followed by removal of certain portions of the coating to form the separate and spaced apart liner and guard structures. In one aspect of the present invention, the guard structure 28 may include a polymeric ribbon formed of silicone material or a ring of such material. The silicone material may have a Modulus of Elasticity or Young's Modulus from about 200 pounds-force per square inch (lbsf/in$^2$) to about 400 lbsf/in$^2$, desirably from about 250 lbsf/in$^2$ to about 350 lbsf/in$^2$. These values are non-limiting and any suitable elasticity modulus may be used. Further, the silicone material may have a Tensile Strength from about 500 lbsf/in$^2$ to about 1,200 lbsf/in$^2$, desirably from about 650 lbsf/in$^2$ to about 970 lbsf/in$^2$. These values are non-limiting and any suitable tensile strength may be used. Additional materials and creep compliances, which is the inverse of the modulus of elasticity, may be found U.S. Pat. No. 6,656,216, which is incorporated in its entirety by reference herein.

Figure 3:
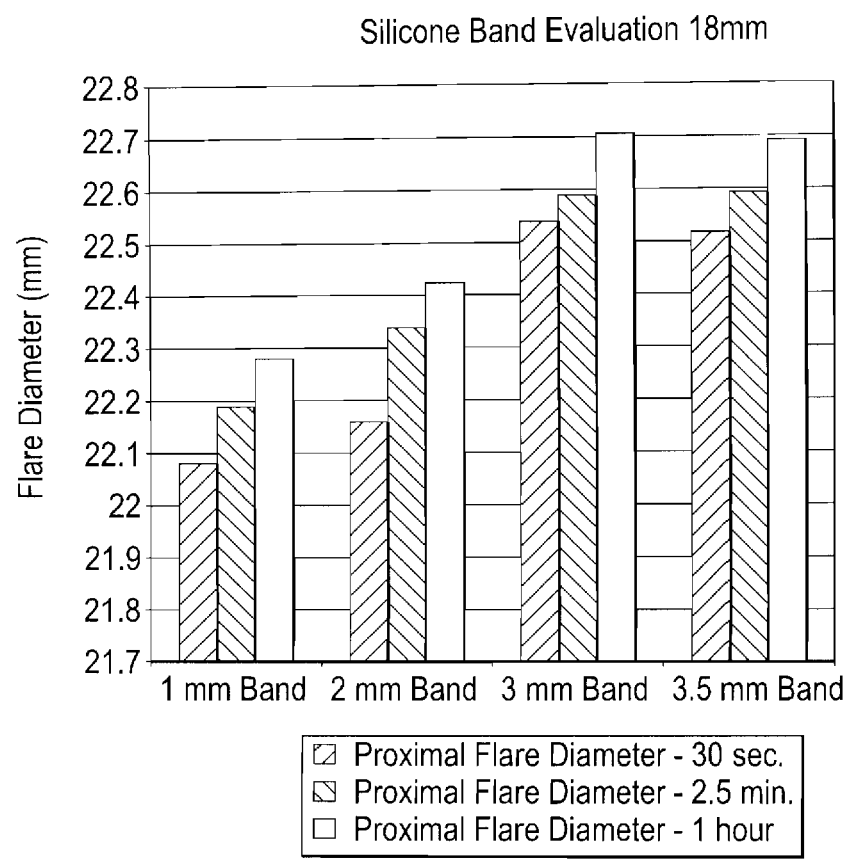
FIG. 3 is a graph showing the test results of the diametrical expansion of a stent structure to which was secured silicone ring structures having different longitudinal dimensions.

The guard structure 28 may have a resilience which is sufficiently limited to resist transverse compression thereof. Consequently, when the guard structure 28 and stent structure 12 are transversely compressed from an original diameter to a reduced diameter, the ring structure urges the stent structure to return to the original diameter. The urging by the guard structure 28 to return the stent structure to the original diameter is indicated by FIG. 3. FIG. 3 shows the results of tests in which a stent structure corresponding to the stent structure 12, and a ring structure corresponding to the guard structure 28 which was secured to the stent structure were subjected to a radial compression force which reduced the diameter thereof. The ring structure was formed of silicone material. Both the stent structure 12 and the guard structure 28 had a nominal diameter of 18 mm in FIG. 3. Subsequently, the radial compression force was removed resulting in an increase in the diameter of the stent structure and a ring structure. The tests were performed for ring structures having longitudinal dimensions (i.e., annulus width) of 1 mm, 2 mm, 3 mm, and 3.5 mm. For each assembly of stent structure and ring structure, measurements of the diameter of the portion of the stent structure to which the ring structure was secured were made 30 seconds, 2.5 minutes, and 1 hour following the removal of the radial compression force from the stent structure and ring structure. FIG. 3 indicates that the stent structures, to which were assembled the ring structures having the increased longitudinal dimensions, radially expanded to the increased diameters. This indicates that the radial expansion of the stent structures was enhanced by the ring structures since the ring structures having the increased longitudinal dimensions, and consequently increased sizes, were assembled to the stent structures which radially expanded to the larger diameters. The proximal flare diameter, as used in FIG. 3, refers the diameter of the flared end of the stent which is proximal to a practitioner during delivery if the stent 12.

Figure 4A:
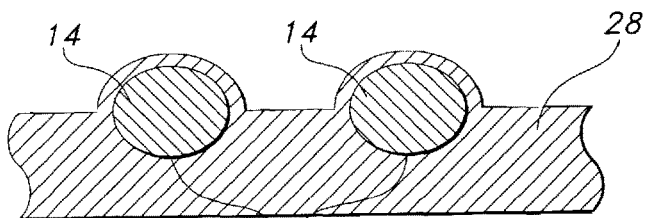
FIG. 4A is a partial cross-sectional view of the stent structure of FIG. 2 taken along the 4A-4A axis.
Figure 4B:
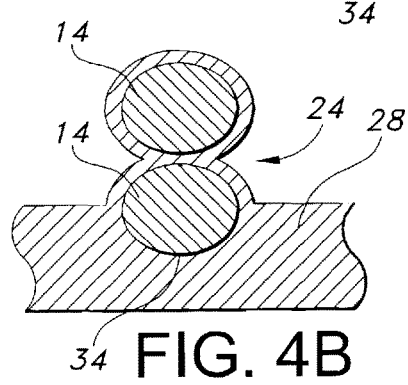
FIG. 4B is a partial cross-sectional view of the stent structure of FIG. 2 taken along the 4B-4B axis.

FIGS. 4A and 4B depict additional details of the guard or ring structure 28 as a coating. As depicted in FIG. 4A, the elongate members or stent filaments 14 may be fully or substantially coated with the coating material of the guard or ring structure 28. A substantial or significant portion of the guard material may be disposed towards the interior portion 34 of the stent structure 12. As depicted in FIG. 4B, the elongate members or stent filaments 14 at stent crossover structures 24 may also be fully or substantially coated with the coating material of the guard or ring structure 28.

Figure 5:
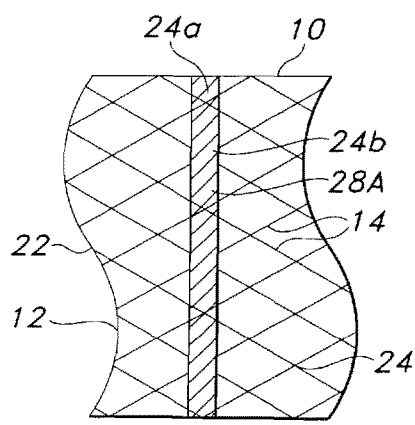
FIG. 5 is a partial planar view of the stent of the present invention showing an interwoven ribbon guard structure.

In one aspect of the present invention as depicted in FIG. 5, the guard structure 28A may be a ribbon of biocompatible material which is interwoven or inter-disposed between the stent wire crossings 24 or the stent wire interstices (e.g., transverse-facing openings, etc.) thereat. For example, the guard structure or ribbon 28A may be disposed under stent wire crossings 24a and over stent wire crossings 24b. Although an alternating pattern of under stent wire crossings 24a and over stent wire crossings 24b is depicted in FIG. 5, the present invention is not so limited. For example, any suitable pattern or interweaving may be used, such as but not limited to crossing over and/or under multiple wire crossings 24. Guard structure 28A need not be a coating, but rather a separate ribbon on material may be used. The ribbon may be disposed among the wire crossings and/or stent wire interstices (e.g., transverse-facing openings, etc.) in any suitable manner.

Figures 6B, 6C:
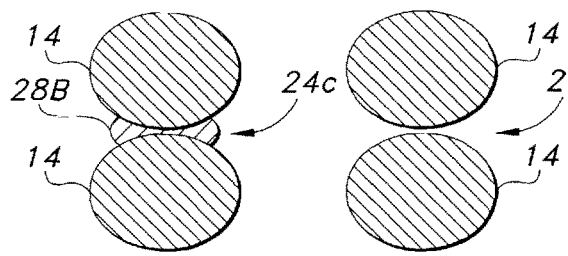
FIG. 6B is a partial cross-sectional view of the stent of the present invention showing the guard structure of FIG. 6A disposed at a wire crossing.
FIG. 6C is a partial cross-sectional view of the stent of the present invention showing a wire crossing without a guard structure.
Figure 6A:
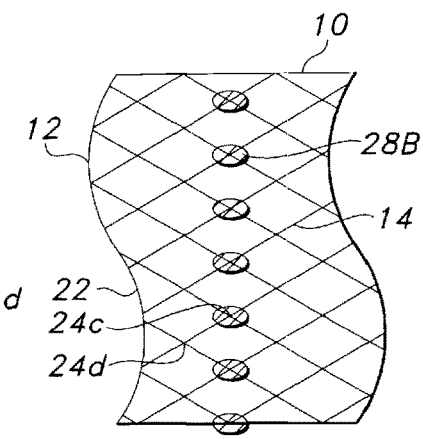
FIG. 6A is a partial planar view of the stent of the present invention showing an embodiment of a guard structure disposed at wire crossings.

In another aspect of the present invention, the guard structure 28 may have a minimal width along the longitudinal dimension of the stent 12. Indeed, the guard structure 28 may just disposed at the wire crossings to secure the wire crossings to each other, thereby preventing the suture structure 26 from becoming entangled thereat. For example, as depicted in FIGS. 6A and 6B, the guard structure 28B may be represented by a small amount of material, such as a bead or the like, disposed at selected wire crossings 24c. As depicted in FIG. 6C, wire crossing 24d not having the guard structure 28B may be free of such guard structure material.

Figure 7:
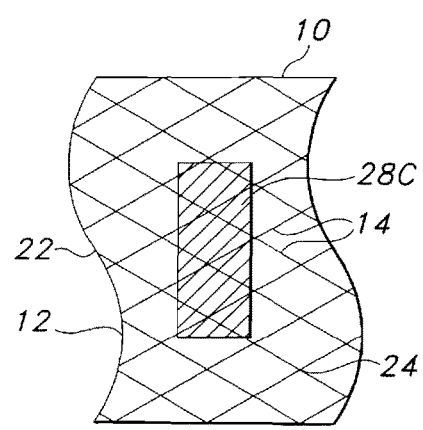
FIG. 7 is a partial planar view of the stent of the present invention depicting a patch-like guard structure.

As depicted in FIG. 7, in yet another aspect or yet another alternative embodiment of the present invention, the ring structure 28 provides for a patch structure 28C to be secured to the stent structure 12 at a location which is adjacent to the crossover structures 24. The patch structure 28C may have an arcuate or other shape and is not required to encircle the entire circumference of the end portion 18. The patch structure 28C obstructs displacement of the suture structure 26 between the overlapping portions of the elongate members 14 which overlap in the crossover structures 24 to which the patch structure 28C is adjacent. The obstruction provided by the patch structure corresponds to the obstruction provided by the ring structure 28 and, consequently, reduces the likelihood of the suture structure 26 becoming entangled with or translating between the overlapping portions of the elongate members 14 in the crossover structures 24. The patch structure may be made from the same materials as the cover or liner 38 or made be made from different material. Although the patch structure 28C is depicted as being rectangular in shape in a planar view, the present invention is not so limited. Any suitable shape for the patch structure 28C may be used.

The guard structure 28 and/or the suture structure 26 may be formed of biocompatible materials, such as biocompatible polymers including those which are known. Such polymers may include fillers such as metals, carbon fibers, glass fibers or ceramics. Also, such polymers may include olefin polymers, polyethylene, polypropylene, polyvinyl chloride, polytetrafluoroethylene which is not expanded, expanded polytetrafluoroethylene (ePTFE), fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the guard structure 28 and/or the suture structure 26.

The stent structure 12, guard structure 28, and/or the suture structure 26 may be treated with a therapeutic agent or agents. The therapeutic agent may be any suitable biologically acceptable agent such as a non-genetic therapeutic agent, a biomolecule, a small molecule, or cells.

Exemplary non-genetic therapeutic agents include anti-thrombogenic agents such as heparin, heparin derivatives, prostaglandin (including micellar prostaglandin E1), urokinase, and PPack (dextrophenylalanine proline arginine chloromethyl ketone); anti-proliferative agents such as enoxaparin, angiopeptin, sirolimus (rapamycin), tacrolimus, everolimus, zotarolimus, biolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc-oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl) ethyleneglycol-N,N,N',N'-tetraacetic acid and mixtures thereof; antibiotics such as gentamicin, rifampin, minocycline, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds including anti-thrombin antibodies, platelet receptor antagonists, anti-platelet receptor antibodies, enoxaparin, hirudin, warfarin sodium, dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; inhibitors of heat shock proteins such as geldanamycin; angiotensin converting enzyme (ACE) inhibitors; beta-blockers; βAR kinase (βSARK) inhibitors; phospholamban inhibitors; protein-bound particle drugs such as ABRAXANE™; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include SERCA 2 protein, monocyte chemoattractant proteins ("MCP-1") and bone morphogenic proteins ("BMPs"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNAs encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathepsin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds that have a molecular weight of less than 100 kD.

Exemplary cells include stem cells, progenitor cells, endothelial cells, adult cardiomyocytes, and smooth muscle cells. Cells can be of human origin (autologous or allogeneic) or from an animal source (xenogeneic), or genetically engineered. Non-limiting examples of cells include side population (SP) cells, lineage negative (Lin$^-$) cells including Lin$^-$ CD34$^-$, Lin$^-$CD34$^+$, Lin$^-$c Kit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, $G_0$ cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may also be incorporated into a polymeric coating on the medical device or a portion of the medical device, or may also be applied onto a polymeric coating on a medical device or a portion of the medical device. The polymers of the polymeric coatings may be biodegradable or non-biodegradable. Non-limiting examples of suitable non-biodegradable polymers include polystyrene; polystyrene maleic anhydride; polyisobutylene copolymers such as styrene-isobutylene-styrene block copolymers (SIBS) and styrene-ethylene/butylene-styrene (SEBS) block copolymers; polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides including poly(methylmethacrylate-butylacetate-methylmethacrylate) block copolymers; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butyl acrylate; polyhydroxybutyrate valerate and blends; polycarbonates such as tyrosine-derived polycarbonates and acrylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropyl methyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc calcium phosphate.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent/therapeutic agent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

With any embodiment, the endoprosthesis 10 and/or stent 12 may be used for a number of purposes including to maintain patency of a body lumen, vessel or conduit, such as in the coronary or peripheral vasculature, esophagus, trachea, bronchi colon, biliary tract, urinary tract, prostate, brain, and the like. The devices of the present invention may also be used to support a weakened body lumen or to provide a fluid-tight conduit for a body lumen.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An endoprosthesis comprising:
   a stent having a first end and a second end, the stent formed of one or more interwoven filaments, wherein portions of the one or more filaments overlap at a plurality of crossover points and define openings through the stent between adjacent crossover points, the stent configured to move between a radially compressed configuration and a radially expanded configuration;
   the stent including a first end region extending to the first end, a second end region extending to the second end, and an intermediate region between the first end region and the second end region;
   a cover disposed along the intermediate region, the cover extending across the openings of the stent throughout the intermediate region; and a guard structure extending circumferentially around the first end region and spaced away from the cover, wherein a first portion of the openings of the stent in the first end region are covered by the guard structure and a second portion of the openings of the stent in the first end region are devoid of any covering, wherein the guard structure urges the stent toward the radially expanded configuration.

2. The endoprosthesis of claim 1, wherein each of the first end region and the second end region has a diameter greater than a diameter of the intermediate region.

3. The endoprosthesis of claim 2, wherein the intermediate region has a constant diameter along its length.

4. The endoprosthesis of claim 1, wherein openings of the stent in second end region are not covered by the cover.

5. The endoprosthesis of claim 1, wherein the guard structure is a polymeric cover separate from and spaced apart from the cover disposed along the intermediate region.

6. The endoprosthesis of claim 5, wherein the guard structure is formed in conjunction with the cover.

7. The endoprosthesis of claim 6, wherein the guard structure is a coating applied to the one or more filaments in the first end region and the cover is a coating applied to the one or more filaments in the intermediate region.

8. The endoprosthesis of claim 1, wherein a circumferential region of the first end region is uncovered.

9. The endoprosthesis of claim 8, wherein the circumferential region is located between the cover and the guard structure.

10. The endoprosthesis of claim 1, wherein the stent includes a plurality of loops formed from the one or more filaments at the first end of the stent.

11. The endoprosthesis of claim 10, wherein the plurality of loops are not covered by the guard structure.

12. The endoprosthesis of claim 11, further comprising a retrieval filament extending through the plurality of loops.

13. An endoprosthesis comprising:
a stent having a first end and a second end spaced longitudinally from the first end, the stent having a braided tubular structure formed of a plurality of interwoven filaments, wherein portions of the plurality of filaments overlap at a plurality of crossover points and define openings through the braided tubular structure between adjacent filaments;
the braided tubular structure including a first end region, a second end region, and an intermediate region between the first end region and the second end region, the intermediate region having a constant diameter from a first end of the intermediate region to a second end of the intermediate region, the first end region extending from the intermediate region to the first end of the stent and the second end region extending from the intermediate region to the second end of the stent, the first end region has a diameter at the first end of the stent greater than the diameter of the intermediate region and the second end region has a diameter at the second end of the stent greater than the diameter of the intermediate region;
a cover disposed only along the intermediate region and extending continuously from the first end of the intermediate region to the second end of the intermediate region, the cover extending across the openings of the braided tubular structure throughout the intermediate region; and
a guard structure extending circumferentially around an entire circumference of the first end region and spaced longitudinally away from the cover with a circumferential uncovered portion of the first end region that is devoid of any covering located between the guard structure and the cover.

14. The endoprosthesis of claim 13, wherein the braided tubular structure includes a plurality of loops formed from the plurality of filaments at the first end of the stent.

15. The endoprosthesis of claim 14, further comprising a retrieval filament extending through the plurality of loops.

16. The endoprosthesis of claim 13, wherein the guard structure is a coating applied to the plurality of filaments in the first end region and the cover is a coating applied to the plurality of filaments in the intermediate region.

17. The endoprosthesis of claim 16, wherein the guard structure is formed in conjunction with the cover.

18. An endoprosthesis comprising:
a stent having a first end and a second end, the stent having a braided tubular structure formed of a plurality of interwoven filaments, wherein portions of the plurality of filaments overlap at a plurality of crossover points and define openings through the braided tubular structure between adjacent filaments, wherein the stent is configured to move between a radially compressed configuration and a radially expanded configuration;
the braided tubular structure including a first end region, a second end region, and an intermediate region between the first end region and the second end region, the intermediate region having a constant diameter from a first end of the intermediate region to a second end of the intermediate region, the first end region extending from the intermediate region to the first end of the stent and the second end region extending from the intermediate region to the second end of the stent, the first end region has a diameter at the first end of the stent greater than the diameter of the intermediate region and the second end region has a diameter at the second end of the stent greater than the diameter of the intermediate region;
a polymeric coating disposed along an entire length of the intermediate region from the first end of the intermediate region to the second end of the intermediate region, the polymeric coating of the intermediate region covering the plurality of filaments and extending across the openings of the braided tubular structure in the intermediate region; and
a polymeric coating extending circumferentially around the first end region and spaced away from the polymeric coating of the intermediate region with a circumferential uncovered portion of the first end region that is devoid of any covering located therebetween, the polymeric coating of the first end region covering the plurality of filaments and extending across openings of the braided tubular structure in the first end region.

19. The endoprosthesis of claim 18, wherein the braided tubular structure includes a plurality of loops formed from the plurality of filaments at the first end of the stent, wherein a retrieval filament extends through the plurality of loops.

20. The endoprosthesis of claim 18, wherein the polymeric coating of the first end region urges the stent toward the radially expanded configuration.

* * * * *